United States Patent [19]
Bui-Bertrand et al.

[11] Patent Number: 5,690,945
[45] Date of Patent: Nov. 25, 1997

[54] COSMETIC SKIN-CLEANSING MASK COMPOSITIONS CONTAINING GRADED SPHEROIDAL POLYAMIDE PARTICLES

[75] Inventors: Lien Bui-Bertrand, Savigny sur Orge; Nathalie Louvet-Plaisant, Chevilly Larue, both of France

[73] Assignee: L'Oreal, Paris, France

[21] Appl. No.: 409,608

[22] Filed: Mar. 24, 1995

[30] Foreign Application Priority Data

Mar. 24, 1994 [FR] France .................... 94 03452

[51] Int. Cl.⁶ .................................................. A61K 7/00
[52] U.S. Cl. .................... 424/401; 514/844; 514/846; 514/944; 514/951
[58] Field of Search ........................ 424/401; 514/844, 514/944, 951, 846

[56] References Cited

U.S. PATENT DOCUMENTS

| | | | |
|---|---|---|---|
| 4,309,411 | 1/1982 | Toida et al. | 424/63 |
| 4,831,061 | 5/1989 | Hilaire et al. | 521/56 |
| 5,057,502 | 10/1991 | Walsh | 424/489 |
| 5,242,689 | 9/1993 | Yoshihara et al. | 424/401 |
| 5,246,780 | 9/1993 | Farer et al. | 424/69 |
| 5,472,699 | 12/1995 | Duffy et al. | 424/401 |

FOREIGN PATENT DOCUMENTS

| | | |
|---|---|---|
| 0 282 823 | 9/1988 | European Pat. Off. . |
| 0 303 530 | 2/1989 | European Pat. Off. . |
| 2563104 | 10/1985 | France . |
| 2 619 385 | 2/1989 | France . |
| 61-171415 | 8/1986 | Japan . |
| 62-043497 | 2/1987 | Japan . |
| 4091018 | 3/1992 | Japan . |

OTHER PUBLICATIONS

Toida et al., Chemical Abstracts, "Preparation of Vinyl Face Masks Containing Titanium Dioxide Modified Nylon 12 Powder", vol. 92, No. 18, (1980).

Derwent Abstract No. 80–02595C of Japanese Patent No. 54/150,549.

Derwent Abstract No. 79–90055B of Japanese Patent No. 54/140,174.

Derwent Abstract No. 83–53012K of Japanese Patent No. 58/069,248.

*Primary Examiner*—Amy Hulina
*Attorney, Agent, or Firm*—Finnegan, Henderson Farabow, Garret & Dunner, L.L.P.

[57] ABSTRACT

A cosmetic skin-cleansing mask composition which contains, as its principal cleansing constituent, graded or calibrated spheroidal polyamide particles which are dispersed in an aqueous gel, the particles being present in an amount greater than or equal to 12% by weight relative to the total weight of the composition.

These particles impart to the composition a texture and qualities which are close to those of a cream.

16 Claims, No Drawings

COSMETIC SKIN-CLEANSING MASK COMPOSITIONS CONTAINING GRADED SPHEROIDAL POLYAMIDE PARTICLES

The present invention relates to a cosmetic composition for use as a cleansing mask comprising, inter alia, as essential cleansing agent, graded or calibrated spheroidal polyamide particles which are dispersed in an aqueous gel. This cosmetic composition constitutes a skin-cleansing product in the form of a mask, which is intended for facial care or for care of a part of the face or of the neck, so as in particular to cleanse the skin deep down, for example by removing the dead cells of the superficial stratum corneum or by removal of the fats which are present in excess on the surface of the skin (sebum, for example), to firm up the skin, to soften it and/or to subject it to a particular treatment. The invention also relates to the use of hollow spheroidal particles in a mask composition and to the use of this composition in a cosmetic treatment.

Products of the beauty mask type are well known in the field of cosmetics. Beauty masks are present in particular in the form of gels, emulsions or pastes. Various formulas for this type of mask are described in the literature, for example in "Cosmetic and Toiletry Formulations", second edition, Ernest W. Flick, 1992. These beauty masks may be moisturizing masks in gel form, which do not have a cleansing function but which provide the skin with a certain degree of comfort. Also known are cleansing masks which, generally, are in the form of an emulsion, and which have the disagreeable feature of imparting to the skin a greasy sensation, and which generally contain a clay-type filler.

All of these types of mask make use in general of a filler in a proportion which does not exceed 10% by weight relative to the total weight of the composition. It is these fillers which, by means of their absorbing power, fix the fatty compounds of the surface of the epidermis (sebum), bringing about a deep-down cleansing of the skin.

Finally, peeling masks exist which are either paste compositions of kaolinite and/or of montmorillonite or film-forming compositions based on polyvinyl alcohol. These peeling masks, after application to the face, dry to give a film which is removed by washing, cleansing or scraping. During the drying time, the stratum corneum is moistened and becomes flexible; moreover, the skin contracts slightly. These masks have the property of absorbing the fats when in contact with the skin, and when they are removed they provide deep-down cleansing of the skin at the same time as a peeling effect which entrains, in particular, the dead cells of the superficial stratum corneum.

These peeling compositions possess the disagreeable feature of having a thick texture in the form of a paste, which is difficult to apply and which dries during the waiting time. This drying induces a pulling effect on the skin of the patient. This astringent effect is perceived as a discomfort.

Moreover, cleansing masks are known which have a high content of kaolin (23%). These masks are present in the form of a paste composition which is applied to the face. During the application time, which is greater than about ten minutes, these compositions dry and likewise bring about pulling of the skin, also causing great discomfort.

Once dry, these masks have the disadvantage of being difficult to remove.

In order to do away with the above disadvantages, the inventors have sought to produce cosmetic compositions which have skin-cleansing qualities which are at least equal to the masks which are known in the cosmetics field, without having the undesirable effects of the conventional emulsions or paste compositions.

In this context, the inventors have surprisingly and unexpectedly found that it was possible to incorporate into aqueous gels a high proportion of a filler consisting essentially of graded or calibrated spheroidal polyamide particles so as to obtain cosmetic compositions which have the appearance of a cream while retaining the intrinsic properties of gels, namely the provision of a pleasant sensation of freshness on application without a greasy effect, which compositions can be used as a skin-cleansing mask. After application to the face for a sufficient time, namely from 5 to 10 minutes, these compositions have the great advantage that they can be removed simply by washing with water and rinsing. Moreover, while having cleansing mask properties, these cosmetic compositions after removal bring about a clearing of the complexion.

Finally, it is possible to note, after application, an optical effect of lessening of the depth of lines.

The graded or calibrated spheroidal polyamide particles which are used in the composition of the invention are known for their use in the cosmetics field in foundations or creams. However, the use concentrations which are recommended in these foundations or creams in no case exceed 10% of the total weight of the composition.

Moreover, Japanese Patent No. 61 249 919 of the company Shiseido teaches the incorporation into gels of organic powders, such as nylon powders, in high proportions of up to 40% by weight. However, the gels used are gels which have a very high content of gelling agent, from 5% to 40% of the total weight of the gel. A product is thus obtained whose texture is similar to that of a thick paste which is mixed by hand before use and which is very unlike the products of creamy appearance which are obtained in accordance with the invention. This product is in fact a cataplasm.

Moreover, the inventors have observed that it was impossible to obtain a cosmetic composition having the properties of those of the invention (creamy appearance, cleansing effectiveness, ease of use and of removal, lack of pulling on the skin) by using, instead of the polyamide particles and in a proportion of greater than 10% of the total weight of the composition, a filler of the kaolin type. Further, since the density of the polyamide particles is markedly greater than that of the conventional additives of cosmetic compositions for cleansing masks, it is in no way obvious to the person skilled in the art to take conventional compositions in gel form, which are used as a base for the masks, and to introduce quantities of polyamide particles which are greater than 12%, while retaining in these compositions the qualities of gels.

The invention therefore relates to a gelled cosmetic composition for use as a cleansing mask. This composition comprises, inter alia, an aqueous gel and, as principal cleansing agent, graded or calibrated spheroidal polyamide particles which are dispersed in this aqueous gel. The particles are present in an amount greater than or equal to 12% by weight relative to the total weight of the composition.

This composition, although having the appearance of a cream, has properties which are very different from those of a care cream. In particular, the effects of a cleansing mask appear after its removal and not during its application to the face, in contrast to a cream.

Moreover, this mask composition does not dry while it is left on and therefore does not bring about pulling of the skin, like the prior art compositions with a high filler content.

In general, the polyamides which are used are listed under the CTFA name "Nylon 12" or "Nylon 6". The polyamide particles which are used in the invention may be those sold under the name "Orgasol" by the company Atochem. The process by which these particles are obtained is, for example, that described in U.S. Pat. No. 4,831,061, in the document FR 2 619 385 or in the document EP 303 530, the disclosures of which are hereby incorporated by reference. These polyamide particles, moreover, are known, according to their various physicochemical properties, under the name "nylon 12" or "nylon 6".

According to the invention, the particles are preferably used in an amount of from 12% to 35% of the total weight of the composition, and more preferably in an amount of from 15% to 20%. Despite the high filler content, the mask composition of the invention is stable for at least 2 months at 45° C., in contrast to what occurs with the other mineral or organic fillers.

The particles used in the invention may also be those sold under the name 8P500 by the company KOBO.

In the compositions according to the invention, the particles have a density which preferably ranges from 1.0 $g/cm^3$ to 1.84 $g/cm^3$ and, more preferably, from 1.02 $g/cm^3$ to 1.4 $g/cm^3$. The particles of the invention are spherical and solid; preferably, they have average dimensions which range from 5 µm to 50 µm and more preferably from 10 µm to 30 µm.

In order to produce the gel on which the composition is based, at least one gelling agent is used in an aqueous liquid vehicle. Of course, the gelling agent is present in a quantity which is sufficient to impart to the composition the desired viscosity. In principle, this viscosity should be greater than 2 Pa.s. By way of example, the gelling agent is introduced into the composition in a proportion which in general ranges from 0.3% to 1% by weight relative to the total weight of the composition, and preferably from 0.5% to 0.8%.

The gelling agents are those which are conventionally used in the cosmetics field, and in particular those chosen from among water-soluble polymers and those which give colloidal solutions in water. These are, in particular, polymers or copolymers of unsaturated carboxylic organic acids or of unsaturated esters, polysaccharide derivatives, gums, colloidal silicates, polyethylene glycols (PEGs) and derivatives thereof, polyvinylpyrrolidones and derivatives thereof, and hydrophilic silica gels.

The gelling agents are, for example, acrylic and/or methacrylic polymers or copolymers, carboxyvinyl polymers, polyglyceryl acrylates or methacrylates, cellulose derivatives, starch derivatives or chitin derivatives, alginates, hyaluronic acid and its salts, chondroitin sulphates, xanthan gum, gellan gum, rhamsan gum, karaya gum or guar gum, carob flour and colloidal silicates of aluminium and magnesium of the montmorillonite type. Specific gelling agents which may be mentioned are in particular: the carboxyvinyl polymers sold under the name Carbopol by the company Goodrich or Synthalen K by the company Sigma, acrylic acid/ethyl acrylate copolymers, acrylic acid/stearyl methacrylate copolymers, the polyglyceryl methacrylate sold under the name Lubrajel by the company Guardian, the polyglyceryl acrylate sold under the name Hispagel by the company Hispano Chimica, carboxymethylcellulose, hydroxymethylcellulose, hydroxypropylcellulose, microcrystalline cellulose, hydroxypropylguar, and the colloidal bentonites or hectorites sold under the name Veegum by the company Van der Bilt.

The compositions of the invention may also contain additional water-soluble or water-solubilized ingredients which are conventionally used in cosmetic compositions, such as polyols, preservatives, moisturizers, fragrances, peptizing agents or fragrance-solubilizing agents such as Cremophor R460 from the company BASF, or castor oil, texturing agents such as pulverulent agents, and dyes. The advantage of the polyols is to improve still further the removal of the mask simply by rinsing. Among the water-soluble or water-solubilized ingredients which can be used, particular mention may be made of propylene glycol, dipropylene glycol, 1,3-butylene glycol, glycerol, polyglycerol, sorbitol, glucose, sucrose, magnesium gluconate, trace elements, and water-soluble silicone-containing acids.

These ingredients are used in proportions which are conventional in the cosmetics field. In particular, the polyols make up from 0.1% to 50% of the total weight of the composition, preferably from 5% to 15%, whereas the other, additional ingredients each make up preferably not more than 2% of the total weight of the composition.

Some compositions of the invention may also contain pulverulent fillers, especially talc, kaolin, clays of the montmorillonite, hectorite or bentonite type, other fillers such as silicas or silicone powders (Tospearl from the company Toshiba) or polymethyl methacrylate powder (Micropearl from the company Matsumoto) in order to obtain optical effects, expanded hollow microspheres (Expancel from the company Kemanord), modified cornstarch powder, or silk powder. These fillers make up less than 5% of the total weight of the composition.

The incorporation of a dispersion of fatty substances into the cosmetic compositions according to the composition may also be envisaged, without going so far as to form an emulsion. These fatty substances may, for example, be fatty acid esters, karite butter, polyoxyethyleneated fatty acid esters, and vegetable and mineral oils.

In order to prepare the compositions according to the invention, the optional additives of the composition (preservatives, etc) and/or the soluble ingredients such as polyols which it is desired to add are dissolved in water at 90° C. The gelling agent is then dispersed in the aqueous solution with vigorous stirring. When the gelling agent is completely dissolved, the temperature is brought to around 50° C. and the polyamide particles are incorporated with vigorous stirring in order to homogenize the mixture. The composition is then cooled before neutralizing its pH (in the vicinity of that of the skin). The composition is colored and perfumed at ambient temperature.

The invention also relates to the use of spheroidal polyamide particles as defined above as additives in a cosmetic composition which has the appearance of a gel and is used as a skin-cleansing mask, especially for the face, in order to impart to it the qualities of a cream.

In addition, the invention also relates to the use of the compositions defined above for the cleansing of facial skin.

Finally, the invention likewise relates to a method of cosmetic treatment, characterized in that a cosmetic composition as defined above is applied to the skin.

Formulas of compositions in accordance with the invention ace now given by way of example but without limitation being implied. The quantities of each constituent are given in per cent by weight.

EXAMPLE 1

| | |
|---|---|
| Orgasol 2002 D | 22% |
| Synthalen K | 0.55% |
| Sodium hydroxide solution | 0.22% |
| 1,3-Butylene glycol | 25% |
| Preservative | 0.3% |

-continued

|  |  |
|---|---|
| Dye | 0.007% |
| Fragrance | 0.2% |
| Peptizing agent | 0.2% |
| Water qs | 100% |

A thick, smooth and shiny cream gel was obtained which was easy to spread, which did not dry while left on (from 5 to 7 minutes) and which therefore did not give a sensation of discomfort (pulling). It was easily removed with water to leave the skin soft, cleansed, and matte.

EXAMPLE 2

|  |  |
|---|---|
| Orgasol 2002 D | 17% |
| Carbopol 980 | 0.5% |
| Triethanolamine | 0.5% |
| Propylene glytol | 20% |
| Preservatives | 0.3% |
| Fragrance | 0.2% |
| Peptizing agent | 0.2% |
| Water qs | 100% |

A thick, smooth and shiny cream gel was obtained which had the same characteristics as that above.

EXAMPLE 3

|  |  |
|---|---|
| SP 500 | 22% |
| Synthalen K | 0.55% |
| Sodium hydroxide solution | 0.22% |
| 1,3-Butylene glycol | 25% |
| Preservatives | 0.3% |
| Fragrance | 0.2% |
| Peptizing agent | 0.2% |
| Water qs | 100% |

A manipulable, smooth and shiny cream was obtained. Its use and effectiveness were identical to those of the two preceding examples.

EXAMPLE 4

|  |  |
|---|---|
| Orgasol 2002 D | 22% |
| Synthalen K | 0.55% |
| Sodium hydroxide solution | 0.22% |
| Preservatives | 0.3% |
| Fragrance | 0.2% |
| Peptizing agent | 0.2% |
| Dye | 0.007% |
| Water qs | 100% |

A thick and smooth cream gel was obtained which was less shiny than that of Example 1; this was because of the absence of glycols.

For comparative tests, the inventors sought to produce compositions according to the invention but replacing, in Example 1, the polyamide powder with kaolin in proportions of 11% and 22% of the weight of the composition. The product obtained turned out to be lumpy and rubbery and did not resemble the gels of creamy appearance which were obtained in accordance with the invention. The product thus obtained did not adhere to the skin and could in no way be used in the cosmetics field. In effect, the introduction of large quantities of filler disrupted the structure of the gel.

What is claimed is:

1. A gelled cosmetic composition for use as a cleansing mask, said composition comprising an aqueous gel and, as principal cleansing agent, graded spheroidal polyamide particles which are dispersed in said aqueous gel, wherein said aqueous gel contains at least one gelling agent present in an amount ranging from 0.3 to 1.0% by weight relative to the total weight of the composition and said particles are present in an amount greater than or equal to 12% by weight relative to the total weight of the composition.

2. A cosmetic composition according to claim 1, wherein the particles are present in an amount which ranges from 12% to 35% by weight relative to the total weight of the composition.

3. A cosmetic composition according to claim 1, wherein the particles have a density which ranges from 1.0 $g/cm^3$ to 1.84 $g/cm^3$.

4. A cosmetic composition according to claim 3, wherein the particles have a density of 1.02 $g/cm^3$ to 1.4 $g/cm^3$.

5. A cosmetic composition according to claim 1, wherein the particles have a size ranging from 5 to 50 µm.

6. A cosmetic composition according to claim 5, wherein the particles have a size ranging from 10 µm to 30 µm.

7. A cosmetic composition according to claim 1, wherein said at least one gelling agent is selected from water-soluble polymers and polymers which give colloidal solutions in water.

8. A cosmetic composition according to claim 1, wherein the gelling agent is selected from polymers and copolymers of unsaturated carboxylic organic acid, polymers and copolymers of unsaturated ester, polysaccharide derivatives, gums, colloidal silicates, polyethylene glycols (PEGs) and derivatives thereof, polyvinylpyrrolidones and derivatives thereof, and hydrophilic silica gels.

9. A cosmetic composition according to claim 1, wherein the gelling agent is selected from acrylic and/or methacrylic polymers and copolymers, carboxyvinyl polymers and copolymers, polyglyceryl acrylates, polyglyceryl methacrylates, cellulose derivatives, starch derivatives, chitin derivatives, alginates, hyaluronic acid and its salts, chondroitin sulphates, xanthan gum, gellan gum, rhamsan gum, karaya gum, guar gum, carob flour, colloidal silicates of aluminium and colloidal silicates of magnesium.

10. A cosmetic composition according to claim 1, characterized in that the gelling agent is present in an amount which ranges from 0.5% to 0.8% of the total weight of the composition.

11. A cosmetic composition according to claim 1, wherein said composition additionally contains water-soluble additives.

12. A cosmetic composition according to claim 11, wherein said water-soluble additives are selected from glycerol, propylene glycol, dipropylene glycol, 1,3-butylene glycol, polyglycerol, sorbitol, glucose, sucrose, magnesium gluconate, trace elements, and water-soluble silicone-containing acids.

13. A cosmetic composition according to claim 1, wherein said composition additionally contains a filler other than said spheroidal polyamide particles.

14. A cosmetic composition according to claim 13, wherein said filler is selected from talc, kaolin, hollow microspheres, modified corn-starch powder, silk powder, clays, silicas, silicone powders, and polymethyl methacrylate powders.

15. A method of cleansing facial skin, comprising the step of applying to the face a cosmetic composition as defined in claim 1.

16. A method of cosmetic treatment, comprising the step of applying to facial skin a cosmetic composition as defined in claim 1.

* * * * *